United States Patent
Trogden et al.

(10) Patent No.: US 9,138,480 B2
(45) Date of Patent: Sep. 22, 2015

(54) COMPOSITIONS AND METHODS FOR STIMULATING HAIR GROWTH

(71) Applicant: Allergan, Inc., Irvine, CA (US)

(72) Inventors: John T. Trogden, Villa Park, CA (US); Adnan K. Salameh, Irvine, CA (US); Chetan P. Pujara, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/163,954

(22) Filed: Jan. 24, 2014

(65) Prior Publication Data

US 2014/0371320 A1    Dec. 18, 2014

Related U.S. Application Data

(63) Continuation of application No. 12/940,711, filed on Nov. 5, 2010, now abandoned.

(60) Provisional application No. 61/259,368, filed on Nov. 9, 2009.

(51) Int. Cl.

| | | |
|---|---|---|
| *A61K 31/5575* | (2006.01) | |
| *A61K 8/34* | (2006.01) | |
| *A61K 8/39* | (2006.01) | |
| *A61K 8/37* | (2006.01) | |
| *A61K 8/36* | (2006.01) | |
| *A61Q 7/00* | (2006.01) | |
| *A61K 47/22* | (2006.01) | |
| *A61K 8/04* | (2006.01) | |
| *A61K 8/42* | (2006.01) | |
| *A61K 31/16* | (2006.01) | |
| *A61K 47/08* | (2006.01) | |
| *A61K 47/10* | (2006.01) | |

(52) U.S. Cl.
CPC .............. *A61K 47/22* (2013.01); *A61K 8/042* (2013.01); *A61K 8/046* (2013.01); *A61K 8/345* (2013.01); *A61K 8/42* (2013.01); *A61K 31/16* (2013.01); *A61K 47/08* (2013.01); *A61K 47/10* (2013.01); *A61Q 7/00* (2013.01); *A61K 2800/87* (2013.01)

(58) Field of Classification Search
CPC .... C07C 405/00; A61K 31/5575; A61K 8/00; A61K 8/34; A61K 8/345; A61K 8/361; A61K 8/375; A61K 8/39; A61Q 7/00
USPC ......... 514/573, 613, 617; 424/70.1, 400, 401; 564/170, 171, 189
See application file for complete search history.

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,008,864 A | 2/1977 | Torphammar et al. |
| 4,014,335 A | 3/1977 | Arnold |
| 4,052,505 A | 10/1977 | Higuchi et al. |
| 4,057,619 A | 11/1977 | Higuchi et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,158,005 A | 6/1979 | Bodor et al. |
| 4,186,184 A | 1/1980 | Zaffaroni |
| 4,190,642 A | 2/1980 | Gale et al. |
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese |
| 4,396,625 A | 8/1983 | Yamamori et al. |
| 4,425,346 A | 1/1984 | Horlington et al. |
| 4,474,451 A | 10/1984 | Mizokami |

(Continued)

FOREIGN PATENT DOCUMENTS

| | | |
|---|---|---|
| CA | 1333770 | 1/1995 |
| CA | 2294714 | 1/1999 |

(Continued)

OTHER PUBLICATIONS

Block, L. H. Medicated Applications, in Remington's Pharmaceutical Sciences; Gennaro, A., Ed., 17th Edition, Mack Publishing Company, Easton PA, 1985; Chapter 88, pp. 1567-1578.*
Acheampong, Andrew, Distribution of Brimonidine Into Anterior and Posterior Tissues of Monkey, Rabbit, and Rat Eyes, The American Society for Pharmacology and Experimental Therapeutics, Jan. 4, 2002, 421-429, 30 (4).
Ahmed, Farid A.K.M. et al, Neuroprotective Effect α2 Agonist (Brimonidine) on Adult Rat Retinal Ganglion Cells After Increased Intraocular Pressure, Brain Research, 2001, 133-139, 913.
Allergan, Alphagan Product Information, Product Sheet, 2005, 1-10.
Allergan, Inc., Tazorac Product Information Sheet, 2004, 1-8.

(Continued)

*Primary Examiner* — Sreeni Padmanabhan
*Assistant Examiner* — Irina Neagu
(74) *Attorney, Agent, or Firm* — Lorenz Siddiqi

(57) ABSTRACT

Methods and compositions for stimulating the growth of hair are disclosed wherein said compositions include a cyclopentane heptanoic acid, 2-cycloalkyl or arylalkyl compound represented by the formula I

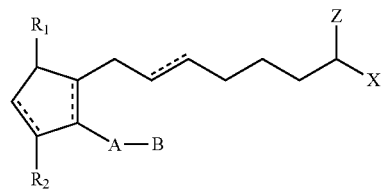

wherein the dashed bonds represent the presence or absence of a double bond which can be in the cis or trans configuration and A, B, Z, X, $R_1$ and $R_2$ are as defined in the specification and a penetration enhancer. Such compositions are used in stimulating hair growth of human or non-human animals.

13 Claims, No Drawings

(56) References Cited

U.S. PATENT DOCUMENTS

| | | |
|---|---|---|
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |
| 4,839,342 A | 6/1989 | Kaswan |
| 4,853,224 A | 8/1989 | Wong |
| 4,863,457 A | 9/1989 | Lee |
| 4,865,846 A | 9/1989 | Kaufman |
| 4,866,168 A | 9/1989 | Dougherty et al. |
| 4,888,354 A | 12/1989 | Chang et al. |
| 4,932,934 A | 6/1990 | Dougherty et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A | 3/1991 | Wong |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,034,413 A | 7/1991 | Chan et al. |
| 5,075,115 A | 12/1991 | Brine |
| 5,089,509 A | 2/1992 | Chandraratna |
| 5,093,349 A | 3/1992 | Pandey et al. |
| 5,100,431 A | 3/1992 | Buster et al. |
| 5,164,188 A | 11/1992 | Wong |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty et al. |
| 5,198,460 A | 3/1993 | Pandey et al. |
| 5,268,178 A | 12/1993 | Calhoun et al. |
| 5,300,114 A | 4/1994 | Gwon et al. |
| 5,314,905 A | 5/1994 | Pandey et al. |
| 5,356,629 A | 10/1994 | Sander et al. |
| 5,378,475 A | 1/1995 | Smith |
| 5,385,887 A | 1/1995 | Yim et al. |
| 5,438,071 A | 8/1995 | Clauss et al. |
| 5,443,505 A | 8/1995 | Wong et al. |
| 5,459,159 A | 10/1995 | Pandey et al. |
| 5,466,233 A | 11/1995 | Weiner et al. |
| 5,474,979 A | 12/1995 | Ding et al. |
| 5,501,856 A | 3/1996 | Ohtori et al. |
| 5,504,074 A | 4/1996 | D'Amato et al. |
| 5,587,371 A | 12/1996 | Sessier et al. |
| 5,587,479 A | 12/1996 | Makovec et al. |
| 5,597,897 A | 1/1997 | Ron et al. |
| 5,632,984 A | 5/1997 | Wong et al. |
| 5,655,832 A | 8/1997 | Pelka et al. |
| 5,656,297 A | 8/1997 | Bernstein et al. |
| 5,688,819 A | 11/1997 | Woodward |
| 5,707,643 A | 1/1998 | Ogura |
| 5,766,242 A | 6/1998 | Wong et al. |
| 5,770,589 A | 6/1998 | Billson et al. |
| 5,776,699 A | 7/1998 | Klein et al. |
| 5,798,349 A | 8/1998 | Levy et al. |
| 5,824,072 A | 10/1998 | Wong |
| 5,824,074 A | 10/1998 | Koch |
| 5,856,329 A | 1/1999 | Wheeler |
| 5,869,079 A | 2/1999 | Wong et al. |
| 5,877,207 A | 3/1999 | Klein et al. |
| 5,882,682 A | 3/1999 | Rork et al. |
| 5,906,920 A | 5/1999 | Evans et al. |
| 5,913,884 A | 6/1999 | Trauner et al. |
| 5,919,970 A | 7/1999 | Song et al. |
| 5,922,773 A | 7/1999 | Lipton et al. |
| 5,958,954 A | 9/1999 | Klein et al. |
| 6,051,576 A | 4/2000 | Ashton et al. |
| 6,066,675 A | 5/2000 | Wen et al. |
| 6,074,661 A | 6/2000 | Olejnik et al. |
| 6,194,415 B1 | 2/2001 | Wheeler |
| 6,203,782 B1 | 3/2001 | Eliaz et al. |
| 6,217,869 B1 | 4/2001 | Meyer et al. |
| 6,217,895 B1 | 4/2001 | Guo et al. |
| 6,225,303 B1 | 5/2001 | Miller et al. |
| 6,248,741 B1 | 6/2001 | Wheeler |
| 6,254,860 B1 | 7/2001 | Garst |
| 6,258,319 B1 | 7/2001 | Hearst et al. |
| 6,270,492 B1 | 8/2001 | Sinofsky |
| 6,270,749 B1 | 8/2001 | Blumenkranz et al. |
| 6,271,220 B1 | 8/2001 | Garst et al. |
| 6,274,614 B1 | 8/2001 | Richter et al. |
| 6,290,713 B1 | 9/2001 | Russell |
| 6,294,361 B1 | 9/2001 | Horowitz et al. |
| 6,306,426 B1 | 10/2001 | Olejnik et al. |
| 6,309,669 B1 | 10/2001 | Setterstrom et al. |
| 6,317,616 B1 | 11/2001 | Glossop |
| 6,319,273 B1 | 11/2001 | Chen et al. |
| 6,331,313 B1 | 12/2001 | Wong et al. |
| 6,350,442 B2 | 2/2002 | Garst |
| 6,357,568 B1 | 3/2002 | Chen |
| 6,369,116 B1 | 4/2002 | Wong et al. |
| 6,403,649 B1 | 6/2002 | Woodward |
| 6,410,045 B1 | 6/2002 | Schultz |
| 6,447,796 B1 | 9/2002 | Vook et al. |
| 6,455,062 B1 | 9/2002 | Olejnik et al. |
| 6,465,464 B2 | 10/2002 | Wheeler et al. |
| 6,482,854 B1 | 11/2002 | Lipton et al. |
| 6,497,729 B1 | 12/2002 | Moussy et al. |
| 6,537,568 B2 | 3/2003 | Olejnik et al. |
| 6,548,078 B2 | 4/2003 | Guo et al. |
| 6,565,871 B2 | 5/2003 | Roser et al. |
| 6,573,280 B2 | 6/2003 | Dreyer |
| 6,595,945 B2 | 7/2003 | Brown |
| 6,692,759 B1 | 2/2004 | Wong et al. |
| 6,699,493 B2 | 3/2004 | Wong |
| 6,713,081 B2 | 3/2004 | Robinson et al. |
| 6,726,918 B1 | 4/2004 | Wong et al. |
| 6,765,012 B2 | 7/2004 | Andrews et al. |
| 7,268,126 B2 | 9/2007 | Liu et al. |
| 7,351,404 B2 * | 4/2008 | Woodward et al. .......... 424/70.1 |
| 7,368,126 B2 | 5/2008 | Chen et al. |
| 7,368,436 B2 | 5/2008 | Gleave et al. |
| 7,589,057 B2 | 9/2009 | Chang et al. |
| 7,714,024 B2 | 5/2010 | Hughes |
| 7,931,909 B2 | 4/2011 | Hughes |
| 8,038,988 B2 * | 10/2011 | Woodward et al. .......... 424/70.1 |
| 8,101,161 B2 * | 1/2012 | Woodward et al. .......... 424/70.1 |
| 8,263,054 B2 * | 9/2012 | Woodward et al. .......... 424/70.1 |
| 8,293,210 B2 | 10/2012 | Huang et al. |
| 8,293,741 B2 | 10/2012 | Burke et al. |
| 8,506,986 B2 | 8/2013 | Huang et al. |
| 8,758,733 B2 | 6/2014 | Ahluwalia et al. |
| 2001/0023363 A1 | 9/2001 | Harth et al. |
| 2001/0049369 A1 | 12/2001 | Jablonski |
| 2002/0010202 A1 | 1/2002 | Garst |
| 2002/0032201 A1 | 3/2002 | Olejnik |
| 2002/0040015 A1 | 4/2002 | Miller et al. |
| 2002/0094998 A1 | 7/2002 | Burke et al. |
| 2002/0111357 A1 | 8/2002 | Wheeler et al. |
| 2003/0018078 A1 | 1/2003 | Woodward et al. |
| 2003/0069286 A1 | 4/2003 | Chen et al. |
| 2003/0069560 A1 | 4/2003 | Adamis et al. |
| 2003/0095995 A1 | 5/2003 | Wong et al. |
| 2003/0157178 A1 | 8/2003 | Chen et al. |
| 2003/0185873 A1 | 10/2003 | Chasin et al. |
| 2003/0199478 A1 | 10/2003 | Andrews et al. |
| 2003/0225152 A1 | 12/2003 | Andrews et al. |
| 2004/0001889 A1 | 1/2004 | Chen |
| 2004/0013704 A1 | 1/2004 | Kabra et al. |
| 2004/0052760 A1 | 3/2004 | Michelet et al. |
| 2004/0054374 A1 | 3/2004 | Weber et al. |
| 2004/0151753 A1 | 8/2004 | Chen et al. |
| 2004/0170665 A1 | 9/2004 | Donovan |
| 2004/0198829 A1 | 10/2004 | Sponsel et al. |
| 2004/0208910 A1 | 10/2004 | Ashton et al. |
| 2004/0266776 A1 | 12/2004 | Gil |
| 2005/0043246 A1 | 2/2005 | Mitra |

(56) References Cited

U.S. PATENT DOCUMENTS

| | | | |
|---|---|---|---|
| 2005/0154399 | A1 | 7/2005 | Weber et al. |
| 2005/0244458 | A1 | 11/2005 | Huang et al. |
| 2005/0244463 | A1 | 11/2005 | Huang |
| 2005/0244467 | A1 | 11/2005 | Nivaggioli et al. |
| 2005/0244476 | A1 | 11/2005 | Burke et al. |
| 2005/0244479 | A1 | 11/2005 | Huang et al. |
| 2005/0244506 | A1 | 11/2005 | Burke et al. |
| 2006/0233860 | A1 | 10/2006 | Chang |
| 2007/0078175 | A1 | 4/2007 | Boulle et al. |
| 2008/0112922 | A1 | 5/2008 | Hughes et al. |
| 2008/0118547 | A1 | 5/2008 | Jackson et al. |
| 2008/0118548 | A1 | 5/2008 | Jackson et al. |
| 2008/0118549 | A1 | 5/2008 | Huang et al. |
| 2008/0131372 | A1 | 6/2008 | Huang et al. |
| 2008/0131485 | A1 | 6/2008 | Huang et al. |
| 2008/0139652 | A1 | 6/2008 | Sakai et al. |
| 2008/0207560 | A1 | 8/2008 | Harada et al. |
| 2008/0260832 | A1 | 10/2008 | Huang et al. |
| 2008/0286334 | A1 | 11/2008 | Shiah et al. |
| 2008/0299178 | A1 | 12/2008 | Huang et al. |
| 2010/0124565 | A1 | 5/2010 | Spada et al. |
| 2011/0251201 | A1 | 10/2011 | Huang et al. |
| 2012/0129789 | A1 | 5/2012 | Yoelin |
| 2012/0251613 | A1 | 10/2012 | Jain et al. |
| 2013/0041025 | A1* | 2/2013 | Walt et al. ............... 514/469 |
| 2014/0155488 | A1* | 6/2014 | Warner et al. ............ 514/622 |
| 2014/0221493 | A1* | 8/2014 | Ahluwalia et al. ....... 514/622 |
| 2014/0371320 | A1 | 12/2014 | Trogden et al. |

FOREIGN PATENT DOCUMENTS

| | | |
|---|---|---|
| EP | 0321870 | 6/1989 |
| EP | 0364417 | 4/1990 |
| EP | 0488401 | 6/1992 |
| EP | 0430539 | 10/1994 |
| EP | 0992244 | 4/2000 |
| WO | 95-13765 | 5/1995 |
| WO | 96-38174 | 12/1996 |
| WO | 01-30323 | 5/2001 |
| WO | 01-58240 | 8/2001 |
| WO | 01-70230 | 9/2001 |
| WO | WO 01/74315 * 10/2001 ............ A61K 7/06 |
| WO | 02-02076 | 1/2002 |
| WO | 02-36162 | 5/2002 |
| WO | 02-43785 | 6/2002 |
| WO | 03-048190 | 6/2003 |
| WO | 03-066008 | 8/2003 |
| WO | 03-077952 | 9/2003 |
| WO | 03-099795 | 12/2003 |
| WO | 2004-066979 | 8/2004 |
| WO | 2005-107705 | 11/2005 |
| WO | 2005-110362 | 11/2005 |
| WO | 2005-110367 | 11/2005 |
| WO | 2005-110368 | 11/2005 |
| WO | 2006-122165 | 11/2006 |
| WO | 2007-074602 | 5/2007 |
| WO | 2007-150018 | 12/2007 |
| WO | 2008-070402 | 6/2008 |
| WO | 2010-056598 | 5/2010 |
| WO | 2011-057129 | 5/2011 |
| WO | 2012-068515 | 5/2012 |
| WO | 2012-112451 | 8/2012 |

OTHER PUBLICATIONS

Alm, Albert et al, Lactate Transport Through the Blood-Retinal and the Blood-Brain Barrier in Rats, Ophthalmic Res., 1985, 181-184, 17.

AlphaganP, Physician's Desk Reference, Product Information, 54th Edition, 493-494, 2001.

Anderson, Lynne et al, An Injectable Sustained Release Fertility Control System, Contraception, 1976, 375-384, 13.

Atluri, Harisha et al, Mechanism of a Model Dipeptide Transport Across Blood-Ocular Barriers Following Systemic Administration, Experimental Eye Research, 2004, 815-822, 78.

Aukunuru, Jithan et al, Expression of Multidrug Resistance-Associated Protein (MRP) in Human Retinal Pigment Epithelial Cells and Its Interaction with BAPSG, a Novel Aldose Reductase Inhibitor, Pharmaceutical Research, 2001, 565-572, 18(5).

Baker, Richard, Controlled Release of Biologically Active Agent, A Wiley, 1987, 73-75, Interscience Publication.

Bartlett, J.D. et al, Contrast Sensitivity Improvements in Brimonidine-Treated Primary Open-Angle Glaucoma Patients Suggest a Neuroprotective Mechanism, ARVO Meeting, 2002, 1 page, Biosis.

Basu, Sujit et al, Proton-Driven Dipeptide Uptake in Primary Cultured Rabbit Conjunctival Epithelial Cells, Invest. Ophthalmol. Vis. Sci., 1998, 2365-2373, 39.

Berger, Urs et al, Distribution of Peptide Transporter PEPT2 mRNA in the Rat Nervous System, Anat. Embryol, 1999, 439-449, 199.

Bergersen, L. et al, Cellular and Subcellular Expression of Monocarboxylate Transporters in the Pigment Epithelium and Retina of the Rat, Neuroscience, 1999, 319-331, 90(1).

Bito, L. Z, Prostaglandins, Other Eicosanoids, and Their derivatives as Potential Antiglaucoma Agents, Glaucoma: Applied Pharmacology, 1984, 477-505, 20.

Bito, LZ, Biological Protection with Prostanoids, CRC Press, Inc., 1985, 231-252, 1, Cohen, M. M., ed., Boca Raton, Fla.

Bito, LZ, Prostaglandins, Old Concepts and New Perspectives, Archives of Ophthalmology, 1987, 1036-1039, 105.

Blazynski, Christine, The Accumulation of [3H]phenylisopropyl Adenosine ([3H]PIA) and [3H]adenosine Into Rabbit Retinal Neurons is Inhibited by Nitrobenzylthioinosine (NBI), Neuroscience Letters, 1991, 1-4, 121.

Bodor, Nicholas et al, A Comparison of Intraocular Pressure Elevating Activity of Loteprednoletabonate and Dexamethasone in Rabbits, Current Eye Research, 1992, 525-530, 11.

Brecha, Nicholas et al, Expression of GAT-1, a High-Affinity Gamma-Aminobutyric Acid Plasma Membrane Transporter in the Rat Retina, The Journal of Comparative Neurology, 1994, 602-611, 345.

Brubaker, Richard, Mechanism of Action of Bimatoprost (LumiganTM), Surv Ophthalmol, 2001, S347-S351, 45—Suppl 4.

Busse, Dagmar et al, Tyrosine Kinase Inhibitors: Rationale, Mechanisms of Action, and Implications for Drug Resistance, Semin Oncol, 2001, 47-55, 28—Suppl 16.

CAS Registry Record from STN-59803-98-4, 1984, 1 Page.

Chancy, Christy et al, Expression and Differential Polarization of the Reduced-Folate Transporter-1 and the Folate Receptor α in Mammalian Retinal Pigment Epithelium, The Journal of Biological Chemistry, 2000, 20676-20684, 275(27).

Charles, Jean-Bernard et al, Use of Bioerodible Polymers Impregnated with Mitomycin in Glaucoma Filtration Surgery in Rabbits, Ophthalmology, Apr. 1991, 503-508, 98-4.

Chen, June et al, LumiganR: A Novel Drug for Glaucoma Therapy, Optom in Pract., Jun. 12, 2002, 95-102, 3.

Cheng, Cheng-Kuo et al., Intravitreal Sustained-Release Dexamethasone Device in the Treatment of Experimental Uveites, Investigative Ophthalmology & Visual Science, 1995, 442-453, 96 (2).

Chiang, Chiao-Hsi et al, Pharmacokinetics and Intraocular Pressure Lowering Effect of Timolol Preparations in Rabbit Eyes, Journal of Ocular Pharmacology and Therapeutics, 1996, 471-480, 12(4).

Cleland, Jeffrey et al, Development of Poly-(D,L-lactide-coglycolide) Microsphere Formulations Containing Recombinant Human Vascular Endothelial Growth Factor to Promote Local Angiogenesis, Journal of Controlled Release, 2001, 13-24, 72.

Clive, Migdal, Lumigan(R): A New Ocular Hypotensive Agent for Achieving Target Intraocular Pressure, ACTA Ophthalmol Scand Scientific Abstracts, 2002, 457, 80-4.

Coleman, Anne et al, A 3-Month Randomized Controlled Trial of Bimatoprost (Lumigan) Versus Combined Timolol and Dorzolamide (Cosopt) in Patients with Glaucoma or Ocular Hypertension, Ophthalmology, 2003, 2362-8, 110-12.

Conti, B. et al, Biodegradable Microspheres for the Intravitreal Administration of Acyclovir In Vitro/In Vivo Evaluation, European Journal of Pharmaceutical Sciences, 1997, 287-293, 5.

(56) References Cited

OTHER PUBLICATIONS

Coquelet, P. et al, Successful Photodynamic Therapy Combined with Laser Photocoagulatio in Three Eyes With Classic Subfoveal Choroidal Neovascularisation Affecting Two Patients With Multifocal Choroiditis: Case Reports, Bull. Soc. Beige Ophthalmal, 2002, 69-73, 283.

Cunha-Vaz, Jose G., The Blood-Ocular Barriers: Past, Present, and Future, Documenta Ophthalmolgica, Advances in Ophthalmology, 1997, 149-157, 93.

De Jong, S.J. et al, New insights into the hydrolytic degradation of poly(lactic acid): participation of the alcohol terminus, Polymer, 2001, 2795-2802, 42.

De, T.K. et al., Brimonidine Formulation in Polyacrylic Acid Nanoparticles for Opthalmic Delivery, Jouranl of Microencapsulation, 2003, 361-374, 20 (3).

Di Colo, Giacomo, Controlled Drug Release From Implantable Matrices Based on Hydrophobic Polymers, Biomaterials, 1992, 850-856, 13(12).

Donello, John E., et al, Alpa2-Adrenoceptor Agonists Inhibit Vitreal Glutamate and Aspartate Accumulation and Preserve Retinal Function after Transient Ischemia, The American Society for Pharmacology and Experimental Therapeutics, 2001, pp. 216-223, vol. 296, No. 1.

Duvvuri, Sridhar et al, Drug Delivery to the Retina: Challenges and Opportunities, Expert Opin Biol Ther, 2003, 45-56, 3(1).

Echeltree, Scott et al, Preliminary Investigation Into the Expression of Proton-Coupled Oligopeptide Transporters in Neural Retina and Retinal Pigment Epithelium (RPE): Lack of Functional Activity in RPE Plasma Membranes, Pharmaceutical Research, Sep. 2003, 1364-1372, 20(9).

Enyedi, Laura et al, An Intravitreal Device Providing Sustained Release of Cyclosporins and Dexamethason, Current Eye Research, 1996, 549-557.

Epstein, David, Primary Open-Angle Glaucoma, Chandler and Grant's Glaucoma, 1986, 129-181.

Evans, D.W. et al, Contrast Sensitivity Improves After Brimonidine Therapy in Primary Open Angle Glaucoma: A Case for Neuroprotection, Br. J. Ophthalmol, 2003, 1463-1465, 87.

Fabbro, Doriano et al, Protein Tyrosine Kinase Inhibitors: New Treatment Modalities?, Current Opinion in Pharmacology, 2002, 374-381, 2.

Fotsis, Theodore et al, The Endogenous Oestrogen Metabolite 2-methoxyoestradiol inhibits Angiogeneses and Suppresses Tumour Growth, Current Opinion in Pharmacology, 1994, 368, 237.

Gandolfi, S.A. et al, Is There a Non IOP-Related Effect of Brimonidine on Visual Field Progression in Human Glaucoma?, Invest Ophthalmol Vis Sci, 2004, E-Abstract 2298, 45.

Gao, Bo et al, Localization of Organic Anion Transport Protein 2 in the Apical Region of Rat Retinal Pigment Epithelium, Invest Ophthalmol Vis Sci, 2002, 510-514, 43.

Gao, Hua et al, Up-Regulation of Brain-Derived Neurotrophic Factor Expressior by Brimonidine in Rat Retinal Ganglion Cells, Arch. Ophthalmol., 2002, 797-803, 120.

George, Ronald et al, Transport of N-Acetylaspartate Via Murine Sodium/Dicarboxylate Cotransporter NaDC3 and Expression of This Transporter and Aspartoacylase II in Ocular Tissues in Mouse, Biochimica et Biophysica Acta, 2004, 63-69, 1690.

Gerhart, D.Z. et al, Distribution of Monocarboxylate Transporters MCT1 and MCT2 in Rat Retina, Neuroscience, 1999, 367-375, 92(1).

Gherzi, Roberto et al, High Expression Levels of the "Erythroid/Brian" Type Glucose Transporter (GLUT1) in the Basal Cells of Human Eye Conjunctiva and Oral Muscosa Reconstituted in Culture, Experimental Cell Research, 1991, 230-236, 195.

Gilman et al, The Pharamceutical Basis of Therapeutics, Goodman and Gilman's, 1990, 1447-1451, 8th Edition.

Goel, Sanjay et al, Tyrosine Kinase Inhibitors: A Clinical Perspective, Current Oncology Reports, 2002, 9-19, 4.

Greenwood, J., Characterization of a Rat Retinal Endothelial Cell Culture and the Expression of P-Glycoprotein in Brain and Retinal Endothelium in Vitro, Journal of Neuroimmunology, 1992, 123-132, 39.

Gu, Sumin et al, Characterization of an N-System Amino Acid Transporter Expressed in Retina and Its Involvement in Glutamine Transport, The Journal of Biological Chemistry, Jun. 2001, 24137-24144, 276(26).

Guenther, Lyn, Optimizing Treatment with Topical Tazarotene, Am. J. Clin. Dermotol, 2003, 197-202, 4-3.

Hainsworth, Dean et al, Sustained Release Intravitreal Dexamethasone, Journal of Ocular Pharmacology and Therapeutics, 1996, 57-63, 12-1.

Haluska, Paul et al, Receptor tyrosine kinase inhibitors, Current Opinion in Investigational Drugs, 2001, 280-286, 2-2.

Hamann, Steffen et al, Cotransport of H+, Lactate, and H2O in Porcine Retinal Pigment Epithelial Cells, Experimental Eye Research, 2003, 493-504, 76.

Han, Yong-Hae et al, Characterization of a Novel Cationic Drug Transporter in Human Retinal Pigment Epithelial Cells, Journal of Pharmacology and Experimental Therapeutics, 2001, 450-457, 296.

Han, Zhiqiang et al, Regulation of Aquaporin-4 Water Channels by Phorbol Ester-Dependent Protein Phosphorylation, The Journal of Biological Chemistry, 1998, 6001-6004, 273(11).

Hare, William et al, Efficacy and Safety of Memantine, an NMDA-Type Open-Channel Blocker, from Reduction of Retinal Injury associated with Experimental Glaucoma in Rat and Monkey, Sur Ophthalmol, 2001, S284-S289, 45—Suppl. 3.

Harik, Sami et al, Glucose Transporters Are Abundant in Cells With "Occluding" Junctions at the Blood-Eye Barriers, Proc. Natl. Acad. Sci., Jun. 1990, 4261-4264, 87.

Hashizoe, Mototane et al, Scleral Plug of Biodegradable Polymers for Controlled Drug Release in the Vitreous, Arch Ophthalmol, 1994, 1380-1384, 112.

Hasson, D. et al, Functional Protection of Rat Retina From Ischemic Injury by Brimonidine, Society for Neuroscience, Oct. 25-30, 1997, 72.4, 23(1).

Heller, J., Hydrogels in Medicine and Pharmacy, N.A. Peppes ed., 1987, 137-149.

Heller, Jorge, Biodegradable Polymers in Controlled Drug Delivery, Critical Reviews in Therapeutic Drug Carrier Systems, 1987, 39-90, 1 (1).

Herrero-Vanrell, Rocio et al, Biodegradable Microspheres for Vitreoretinal Drug Delivery, Advanced Drug Delivery, 2001, 5-16, 52.

Honda, Shigeru et al, Immunocytochemical Localization of Three Subtypes of GABA Transporter in Rat Retina, Molecular Brain Research, 1995, 319-325, 33.

Horibe, Yoshihide et al, Carrier-Mediated Transport of Monocarboxylate Drugs in the Pigmented Rabbit Conjunctiva, Invest Ophthalmol Vis Sci, 1998, 1436-1443, 39.

Horibe, Yoshihide et al, Kinetic Evidence for Na+-Glucose Co-Transport in the Pigmented Rabbit Conjunctiva, Current Eye Research, 1997, 1050-1055.

Horibe, Yoshihide et al, Polar Soluted Transport Across the Pigmented Rabbit Conjunctiva: Size Dependence and the Influence of 8-Bromo Cyclic Adenosine Monophosphate, Pharmacutical Research, 1997, 1246-1251, 14(9).

Hosoya, Ken-Ichi et al, Contribution of Na+-glucose Cotransport tot he Short-Circuit Current in the Pigmented Rabbit Conjunctiva, Current Eye Research, 1996, 447-451, 15.

Hosoya, Ken-Ichi et al, MCT1-Mediated Transport of L-Lactic Acid at the Inner Blood-Retinal Barrier: A Possible Route for Delivery of Monocarboxylic Acid Drugs to the Retina, Pharmaceutical Research, Dec. 2001, 1669-1676, 18(12).

Hosoya, Ken-Ichi et al, Na+-Dependent L-Arginine Transport in the Pigmented Rabbit Conjunctiva, Exp Eye Res, 1997, 547-553, 65.

Hosoya, Ken-Ichi et al, Nucleoside Transport Mechanisms in the Pigmented Rabbit Conjunctiva, Invest Ophthalmol Vis Sci, 1998, 372-377, 39.

Hoyng, Philip et al, Pharmacological Therapy for Glaucoma, Drugs 2000, 2000, 411-434, 59 (3).

(56) References Cited

OTHER PUBLICATIONS

Hu, M. et al, Expression of GABA Transporter Subtypes (GAT1, GAT3) in the Developing Rabbit Retina, Acta Ophthalmol. Scand., 1999, 261-265, 77.

Hubbard, Stevan et al, Protein Tyrosine Kinase Structure and Function, Annu. Rev. Biochem., 2000, 373-98, 69.

Inoue, Kiyoshi et al, Cloning and Expression of a Bovine Glutamate Transporter, Molecular Brain Research, 1995, 343-348, 28.

Ito, Aki et al, Distribution of Organic Anion-Transporting Polypeptide 2 (oatp2) and oatp3 in the Rat Retina, Invest Ophthalmol Vis Sci, 2002, 858-863, 43.

Ito, Aki et al, Distribution of Rat Organic Anion Transporting Polypeptide-E (oatp-E) in the Rat Eye, Invest Ophthalmol Vis Sci, 2003, 4877-4884, 44.

Jackanicz, Theodore et al, Polyactic Acid as a Biodegradable Carrier for Contraceptive Steroids, Contraception, 1973, 227-235, 8-3.

Jampel, Henry et al, Glaucoma Filtration Surgery in Monkeys Using 5-Fluorouridine in Polyanhydride Disks, Arch Ophthalmol, Mar. 1990, 430-435, 108.

John Wiley, Encyclopedia of polymer science and Engineering, 1985, vol. 3.

Kennedy, Brian et al, P-Glycoprotein Expression in Human Retinal Pigment Epithelium, Molecular Vision, 2002, 422-430, 8.

Kenyon, Emily et al, Lactate Transport Mechanisms at Apical and Basolateral Membranes of Bovine Retinal Pigment Epithelium, Am J Physiol, 1994, C1561-C1578, 267.

Kim, In-Beom et al, Immunocytochemical Localization of Aquaporin 1 in the Rat Retina, Neuroscience Letters, 1998, 52-54, 244.

Kimura, Hideya et al, A New Vitreal Drug Delivery System Using an Implantable Biodegradable Polymeric Device, Invest Ophthalmol Vis Sci, 1994, 2815-2819, 35.

Knott, R.M. et al, A Model System for the Study of Human Retinal Angiogenesis: Activation of Monocytes and Endothelial Cells and the Association with the Expression of the Monocaroxylate Transporter Type 1 (MCT-1), Diabetologica, 1999, 870-877, 42.

Knott, R.M. et al, Regulation of Glucose Transporter (GLUT 3) and Aldose Reductase mRNA in Bovine Retinal Endothelial Cells and Retinal Pericytes in High Glucose and High Galactose Culture, Diabetologica, 1993, 808-812, 36.

Kochinke, F. et al, Biodegradable Drug Delivery System for Uveitis Treatment, Investigative Ophthalmology & Visual Science, Feb. 15, 1996, 186-B98, 37(3).

Kompella, Udaya Bhaskar et al, Possible Existence of Na+-Coupled Amino Acid Transport in the Pigmented Rabbit Conjuctiva, Life Sciences, 1995, 1427-1431, 57(15).

Kwak, Hyung Woo et al, Evaluation of the Retinal Toxicity and Pharmacokinetics of Dexamethasone After Intravitreal Injection, Arch. Ophthalmol, 1992, 259-66, 110.

Lai, Ronald et al, Alpha-2 Adrenoceptor Agonist Protects Retinal Function After Acute Retinal Ischemic Injury in the Rat, Vis Neurosci, 2002, 175-185, 19.

Lee, David et al, Glaucoma Filtration Surgery in Rabbits Using Bioerodible Polymers and 5-Fluorouacil, Ophthalmol, Dec. 1987, 1523-1530, 94-12.

Lee, David et al, The Use of Bioerodible Polymers and 5-Fluorouracils in Glaucoma Filtration Surgery, Ophthalmology & Visual Science, Nov. 1988, 1692-1697, 29-11.

Lee, Susan et al, Biodegradable Implants for Sustained Drug Release in the Eye, Pharm Res, 2010, 2043-2053, 27.

Lewis, Danny, Controlled Release of Bioactive Agents from Lactide/ Glycolide Polymers, Biodegradable Polymers as Drug Delivery Systems, 1990, 1-35, 45.

Macular Degeneration Genetics, Oct. 31, 2006, http://macular-degeneration.emedtv.com/macular-degeneration/macular-degeneration-genetics.html, 1 Page.

Majumdar, Soumyajit et al, Mechanism of Ganciclovir Uptake by Rabbit Retina and Human Retinal Pigmented Epithelium Cell Line ARPE-19, Current Eye Research, 2004, 127-136, 29(2-3).

Mantych, Gregory et al, Characterization of Glucose Transporter Isoforms in the Adult and Developing Human Eye, Endocrinology, 1993, 600-607, 133(2).

Marks, R., Topical Tazarotene:Review and Re-Evaluation, Retinoids, 2001, 72-74, 17(3).

Maurice, David, Micropharmaceutics of the Eye, Ocular Inflammation Ther., 1983, 97-102, 1.

Mayo Clinic Com, Stargardt's Disease: Can It Be Treated?, May 27, 2008, 2 Pages.

Merck Manuals, Retinitis Pigmentosa, 2005, http://merck.com/mmpe/print/sec09/ch106/ch106h.html, printed May 27, 2008. 2 Pages.

Merkli, Alain et al, Use of Insoluble Biodegradable Polymers in Ophthalmic Systems for the Sustained Release of Drugs, European Journal of Pharmaceutics and Biopharmaceutics, 1995, 271-283, 41 (5).

Miller, Robert et al, Degradation Rats of Oral Resorbable Implants (Polyactates and Polyglycolates): Rate Modification with Changes in PLA/PGA Copolymer Ratios, J. Biomed Materials Res, 1977, 711-719, 11.

Miller, Thomas et al, Synthesis and Structure-Activity Profiles of A-Homoestranes, the Estratopones, J. Med. Chem., 1997, 3836-3841, 40.

Mondal, L.K. et al, The Efficacy of Topical Administration of Brimonidine to Reduce Ischaemia in the Very Early Stage of Diabetic Retinopathy in Good Controlled Type-2 Diabetes Mellitus, J India Med Assoc, 2004, 724-729, 102.

Newman, Hereditary Optic Neuropathis: From the Mitochondria to the Optic Nerve, American Journal of Ophthalmology, 2005, 517e1-517e8, 140(3).

Oculex, Oculex Announces Positive Clinical Results for Posurdex(r) the first biodegradable ocular implant, PR Newswire, Aug. 6, 2002, 1-2.

Olsen, Timothy et al, Human Scleral Permeability: Effects of Age, Cryotherapy, Transcleral Diode Laser, and Surgical Thinning, Invest. Ophthalmol. Vis. Sci., 1995, 1893-1903, 36.

Patil, Rajkumar et al, Expression of Aquaporins in the Rat Ocular Tissue, Exp Eye Res, 1997, 203-209, 64.

Peterson, Ward et al, Identification and Functional Characterization of a Dual GABA/Taurine Transporter in the Bullfrog Retinal Pigment Epithelium, J. Gen. Physiol., Dec. 1995, 1089-1122, 106.

Phillips, Calbert et al, Penetration of Timolol Eye Drops into Human Aqueous Humor: The First Hour, British Journal of Ophthalmology, 1985, 217-218, 69.

Phillips, Tania et al, Efficacy of 0.1% Tazarotene Cream for the treatment of Photodamage, Arch Dermatol, Nov. 2002, 1486-1493, 138(11).

Philp, Nancy et al, Monocarboxylate Transporter MCT1 is Located in the Apical Membrane and MCT3 in the Basal Membrane of Rat RPE, Am. J. Physiol., 1998, R1824-R1828, 43.

Philp, Nancy et al, Polarized Expression of Monocarboxylate Transporters in Human Retinal Pigment Epithelium and ARPE-19 Cells, Invest Ophthalmol Vis Sci, 2003, 1716-1721, 44.

Physician's Desk Reference for Ophthalmic Medicines, 30th Edition, 285-294, 2002.

Pignataro, Leonardo et al, Nonsynaptic Localization of the Excitatory Amino Acid Transporter 4 in Photoreceptors, Mol. Cell. Neurosci., 2005, 440-451, 28.

Pribluda, Victor et al, 2-Methoxyestradiol: An Endogenous Antiangionic and Antiproliferative Drug Candidate, Cancer and Metastasis Reviews, 2000, 173-179, 19.

Quigley, Harry et al, The Mechanism of Optic Nerve Damage in Experimental Acute Intraocular Pressure Elevation, Invest Ophthalmol. Vis. Sci., 1980, 505-517, 19.

Rajan, Prasanna et al, Expression of the Extraneuronal Monoamine Transporter in RPE and Neural Retina, Current Eye Research, 2000, 195-204, 20(3).

Rao et al, Intraocular Inflammation and Uveitis, Basic and Clinical Science Course; Intraocular Inflammation and Uveitis, 1998-1999, 57-80; 102-103; 152-156, Section 9; Part 2.

Rauen, T., Diversity of Glutamate Transporter Expression and Function in the Mammalian Retina, Amino Acids, 2000, 53-62, 19.

(56) References Cited

OTHER PUBLICATIONS

Renfro, Lisa et al, Ocular Effects of Topical and Systemic Steroids, Dermatologic Clinics, 1992, 505-512, 10.
Roff, W.J. et al, Fibres, Films, Plastics and Rubbers, A Handbook of Common Polymers, 1971, 7 Pages, 1.
Rowe, Raymond et al, Aliphatic Polyesters, Handbook of Pharmaceutical Excipients, Nov. 2003, 19-21, 4th Edition.
Ruiz, Maria et al, Cloning, Expression, and Localization of a Mouse Retinal γ-Aminobutyric Acid Transporter, Invest Ophthalmol Vis Sci, 1994, 4039-4048, 35.
Saba, Pratik et al, Existence of a p-Glycoprotein Drug Efflux Pump in Cultured Rabbit Conjunctival Epithelial Cells, Invest Ophthalmol Vis Sci, 1998, 1221-1226, 39.
Schmidt-Erfurth, Ursula et al, Management of Neovascular Age-Related Macular Degeneration, Progress in Retinal and Eye Research, 2007, 437-451, 26.
Schonfeld, David, Lumigan Found Effective in Early Phase 3, Ocul. Surg. News, Mar. 1, 2001, 35, 19(5)1.
Schuettauf, Frank et al, Effects of anti-glaucoma Medications on Ganglion Cell Survival: the DBA/2J Mouse Model, Vision Res., 2002, 2333-2337, 42(20).
Schumacher, Guido et al, The Physiological Estrogen Metabolite 2-Methoxyestradiol Reduced Tumor Growth and Induces Apoptosis in Human Solid Tumors, J Cancer Res Clin Oncol, 2001, 405-410, 127.
Schwartz, Bernard, The Response of Ocular Pressure to Corticosteroids, Ophthamol. Clin. North Am., 1966, 929-989, 6.
Shi, Xiao-Ping et al, Active Sodium and Chloride Transport Across the Isolated Rabbit Conjunctiva, Current Eye Research, 1995, 927-935, 14.
Siebold et al., Esterified Prostaglandin Shows 'Potent' Promise, Ocular Surgery News, Feb. 1, 1989, pp. 3, 59, 1.
Skalka, Harold et al, Effect of Corticosteroids on Cataract Formation, Arch. Ophthalmol, 1980, 1773-1777, 98.
Smith, Thomas et al, Sustained-Release Subconjunctival 5-Fluorouracil, Ophthalmic Surgery and Laser, Sep. 1996, 763-767, 27-9.
Starr, Michael, Further Studies on the Effects of Prostagladin on Intraocular Pressure in the Rabbit, Exp. Eye Res., 1971, 170-177, 11.
Steuer, Heiko et al, Functional Characterization and Comparison of the Outer Blood-Retina Barrier and the Blood-Brain Barrier, Invest Ophthalmol Vis Sci, 2005, 1047-1053, 46.
Tazarotene, Drugs Future, 208-209-2003.
Tenckhoff, Solveig et al, Diversity of Aquaporin mRNA Expressed by Rat and Human Retinas, NeuroReport, 2005, 53-56, 16.
To, Chi Ho et al, The Saturation Characteristics of Glucose Transport in Bovine Retinal Pigment Epithelium, Eye Science, 1998, 126-129, 14(3).
Tornquist, P. et al, Carrier-Mediated Transport of Amino Acids Through the Blood-Retinal and the Blood-Brain Barriers, Graefe's Arch Clin Exp Ophthalmol, 1986, 21-25, 224.
Tracy, M.A. et al, Factors Affecting the Degradation Rate of Poly(actide-co-glycolide) Microspheres in Vivo and in Vitro, Biomaterials, 1999, 1057-1062, 20.
Tsukamoto, Hidetoshi et al, Isoforms of Glucose Transporter in the Iris-Cillary Body, Jpn J Ophthalmol, 1995, 242-247, 39.
Ueda, Hideo et al, Functional Characterization of Organic Cation Drug Transport in the Pigmented Rabbit Conjunctiva, Invest Ophthalmol Vis Sci, 2000, 870-876, 41.
United States Pharmacopeia, The National Formulary, USP23, 1995, 1790-1798, 18.
Vijayasarathy, Camasamudram et al, Identification and Characterization of Two Mature Isoforms of Retinoschisin in Murine Retina, Biochemical and Biophysical Research Communications, 2006, 99-105, 349, US.
Walters et al, Expression, transport properties, and chromosomal location of organic anion transporter subtype 3, Am J Physiol Gastrointest Liver Physiol, 2000, G1188-G1200, 279.
Watanabe, Takashi et al, GLUT2 Expression in the Rat Retina: Localization at the Apical Endsof Muller Cells, Brain Research, 1994, 128-134, 655.
Watson, Peter et al, A Six-month, Randomized Double-masked Study Comparing Latanoprost with Timolol in Open-Angle Glaucoma and Ocular Hypertension, Ophthalmology, 1996, 126-137, 103.
Wheeler, L.A. et al, Alpha-2adrenergic Receptor Agonists Are Neuroprotective in Experimental Models of Glaucoma, Eur J Ophthalmol, 2001, S30-S35, 11(Suppl 2).
Wheeler, Larry et al, Role of Alpha-2 Adrenergic Receptors in Neuroprotection and Glaucoma, Surv Ophthalmol, May 2001, S290-S294, vol. 45, Supplement 3.
Wheeler, Larry, Experimental Study of Agents with Potential Neuroprotective Properties, Acta Ophthalmol Scand, 1999, 27-28, 77.
Williams, Evans et al, Nucleoside Transport Sites in a Cultured Human Retinal Cell Line Established by SV-401 T Antigen Gene, Current Eye Research, 1994, 109-118, 13.
Woldemussie, Elizabeth et al, Neuroprotection Effects of Memantine in Different Retinal Injury Models of Glaucoma, J Glaucoma, 2002, 474-480, 11(6).
Woldemussie, Elizabeth, Neuroprotection of Retinal Ganglion Cells in Experimental Models of Glaucoma, Minerva Ophthalmol, 2000, 71-78, 42(2).
Woodward, David et al, AGN 192024 (LumiganR): A Synthetic Prostamide Analog that Lowers Primate Intraocular Pressure by Virtue of Its Inherent Pharmacological Activity, ARVO, 2002, 1 p. (Abstract), 43.
Woodward, David et al, Pharmacology of Bimatoprost (LumiganTM), Survey of Ophthalmology, May 2001, S337-S345, vol. 45.
Yasukawa, T. et al., Biodegradable Scleral Plugs for Vitreoretinal Drug Delivery, Advanced Drug Delivery Reviews, 2001, 25-36, 52, US.
Zhao, Jing-Wei et al, Expression of GABA Transporters on Bullfrog Retinal Muller Cells, GLIA, 2000, 104-117, 31.
Zhao, Jing-Wei et al, Glutamate Transporter EAAC1 Is Expressed on Muller Cells of Lower Vertebrate Retinas, Journal of Neuroscience Research, 2001, 89-95, 66.
Zhou, Tianhong et al, Development of a Multiple-Drug Delivery Implant for Intraocular Management of Proliferative Vitreoretinopathy, Journal of Controlled Release, 1998, 281-295, 55.
Masaru, Tagima et al, Status and Problem of Products for Hair and Makeup, Fragrance Journal, Jan. 15, 1997, 46, 25(1), Japan.
Sigeru, Sekine et al, Handbook of Cosmetics, Oct. 30, 2006, 714, Nikko Chemicals Co. Ltd., Japan.
Williams, Adrian et al, Penetration Enhancers, Advanced Drug Delivery Reviews, 2004, 603-618, 56.
Jover, Eric et al, Comparative Characterization of a Wool-Wax Extract by Two Complementary Chromatographic Techniques, J Cosmet Sci, Jan./Feb. 2006, 23-35, 57.
Wolfmeier et al, Waxes, in Ullmann's encyclopedia of industrial chemistry, Jun. 15, 2000, 111-172, 39.

* cited by examiner

COMPOSITIONS AND METHODS FOR STIMULATING HAIR GROWTH

RELATED APPLICATION

This application is a continuation of U.S. patent application Ser. No. 12/940,711, which claims the benefit of U.S. Provisional Patent Application No. 61/259,368, filed Nov. 9, 2009, each of which is hereby incorporated by reference in its entirety.

FIELD OF THE INVENTION

Disclosed herein are compositions and methods for stimulating the growth of hair and treating disorders resulting in hair loss wherein said compositions include a cyclopentane heptanoic acid, 2-cycloalkyl or arylalkyl compound represented by the formula I:

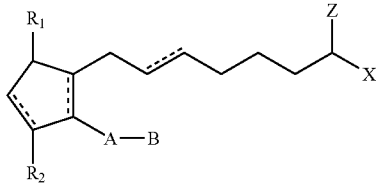

wherein the dashed bonds represent the presence or absence of a double bond which can be in the cis or trans configuration and A, B, Z, X, $R_1$ and $R_2$ are as defined in the specification and a penetration enhancer. Such compositions are used in stimulating hair growth of human or non-human animals.

BACKGROUND OF THE INVENTION

Dermatologists recognize many different types of hair loss, the most common being "alopecia" or "baldness" wherein humans (mostly males) begin losing scalp hair at the temples and on the crown of their head. However, hair loss may be due to many other disorders.

Hair loss is often accompanied by a change in the hair growth cycle. All mammalian hair passes through a life cycle that includes the anagen phase, the catagen phase and the telogen phase. The anagen phase is the period of active hair growth. In the scalp, this phase lasts from 3-5 years. The catagen phase is a short 1-2 week transitional phase between the anagen phase and the telogen phase. The final telogen phase is considered a "resting phase" where all growth ceases. This phase is also relatively short-lived lasting about 3-4 months before the hair is shed and a new one begins to grow. With the onset of baldness, a successively greater proportion of hairs are in the telogen phase with correspondingly fewer in the active growth anagen phase.

Additionally, different types of hair exist including terminal hairs, vellus hairs and modified terminal hairs. Terminal hairs are coarse, pigmented, long hairs in which the bulb of the hair follicle is seated deep in the dermis. Vellus hairs, on the other hand, are fine, thin, non-pigmented short hairs in which the hair bulb is located superficially in the dermis. Modified terminal hairs are seen in eye lashes and eye brows. As alopecia progresses, a transition takes place wherein the hairs themselves change from the terminal to the vellus type. Accordingly, alopecia (baldness) also includes a deficiency in terminal hairs.

One non-drug treatment for alopecia is hair transplantation. Plugs of skin containing hair are transplanted from areas of the scalp where hair is growing to bald areas. This approach can be reasonably successful; however it is costly, time-consuming and painful. Other non-drug related approaches to treating alopecia include ultra-violet radiation, massage, psychiatric treatment and exercise therapy. None of these approaches, however, have been generally accepted as effective. Even such things as revascularization surgery or acupuncture have shown little, if any, effect.

SUMMARY OF THE INVENTION

Compositions and methods are disclosed herein for topical application of an effective amount of at least one penetration enhancer and cyclopentane heptanoic acid, 2-cycloalkyl or arylalkyl compound represented by the formula I:

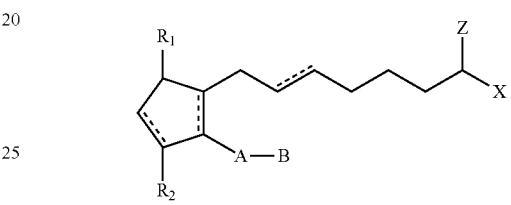

wherein the dashed bonds represent the presence or absence of a double bond which can be in the cis or trans configuration, A is an alkylene or alkenylene radical having from two to six carbon atoms, which radical can be interrupted by one or more oxo radicals and substituted with one or more hydroxy, oxo, alkyloxy or alkylcarboxy groups wherein the alkyl radical comprises from one to six carbon atoms; B is a cycloalkyl radical having from three to seven carbon atoms, or an aryl radical, selected from the group consisting of hydrogen, a lower alkyl radical having from four to ten carbon atoms wherein the heteroatom is selected from the group consisting of nitrogen, oxygen and sulfur atoms; X is —N($R_4$)$_2$ wherein $R_4$ is selected from the group consisting of hydrogen, a lower alkyl radical having from one to six carbon atoms,

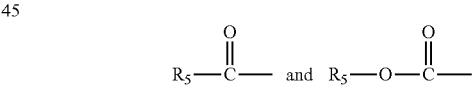

wherein $R_5$ is a lower alkyl radical having from one to six carbon atoms; Z is =O; one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)m$R_7$ wherein m is 0 or an integer of from 1 to 10, and $R_7$ is cycloalkyl radical, having from three to seven carbon atoms, or a hydrocarbyl aryl or heteroaryl radical, as defined above in free form or a pharmaceutically acceptable salt thereof, in association with a penetration enhancer in particular formulations adapted for topical application to mammalian skin.

In one embodiment, the cyclopentane heptanoic acid, 2-cycloalkyl or arylalkyl compound represented by the formula I is the compound bimatoprost.

Another embodiment includes a composition comprising bimatoprost at a concentration of about 0.001-1.5% w/w, from 0.01-1.0% w/w, from 0.02-1.0% w/w, 0.03 to about 1.0% w/w, 0.03 to 0.9% w/w, 0.04 to 0.8% w/w, 0.05-0.7% w/w, 0.06%-0.6% w/w, 0.07%-0.5% w/w, 0.08-0.4% w/w, 0.09-0.3% w/w, 0.1% w/w, 0.2% w/w, 0.3% w/w, 0.4% w/w, 0.5% w/w, 0.6% w/w, 0.7% w/w, 0.8% w/w, 0.9% w/w and 1.0% w/w. The following excipients maybe also be included: Carbomer at a concentration of about 0.05-1.0% w/w; base at a concentration of about 0.01 to about 2.0% w/w; ethanol at a concentration of about 10 to about 90% w/w; glycerin at a concentration of about 1.0 to about 20% w/w; diethylene glycol monoethyl ether at a concentration of about 1.0 to about 50% w/w; polysorbate 20 at a concentration of about 0.1 to about 5.0% w/w; polysorbate 40 at a concentration of about 0.1 to about 5.0% w/w; polysorbate 60 at a concentration of about 0.1 to about 5.0% w/w; polysorbate 80 at a concentration of about 0.1 to about 5.0% w/w; PPG-5 ceteth-20 at a concentration of about 0.1 to about 5.0% w/w; oleic acid at a concentration of about 0.1 to about 5.0% w/w; isostearyl isostearate at a concentration of about 0.1 to about 10% w/w; isopropyl myristate at a concentration of about 0.1 to about 10% w/w; dipropylene glycol dimethyl ether at a concentration of about 1 to about 50% w/w; diethylene glycol at a concentration of about 1 to about 50% w/w; dipropylene glycol at a concentration of about 1 to about 50% w/w; caprylic/capric at a concentration of about 0.1 to about 10% w/w; benzyl alcohol at a concentration of about 0.1 to about 2.0% w/w; silicone at a concentration of about 0.1 to about 10% w/w; and/or water at a concentration of about 0 to about 90% w/w.

Another embodiment includes a composition comprising bimatoprost at about 0.1% w/w; carbomer at about 0.10% w/w; NaOH at about 0.035% w/w; ethanol at about 15.0% w/w; diethylene glycol monoethyl ether at about 10.0% w/w; and water at about 74.8% w/w.

Another embodiment includes a composition comprising bimatoprost at about 0.1% w/w; carbomer at about 0.15% w/w; triethylamine (TEA) at about 0.22% w/w; ethanol at about 15.0% w/w; diethylene glycol monoethyl ether at about 10.0% w/w; polysorbate 20 at about 4.0% w/w; and water at about 70.5% w/w.

Another embodiment includes a composition comprising bimatoprost at about 0.1% w/w; carbomer at about 0.125% w/w; TEA at about 0.18% w/w; ethanol at about 30.0% w/w; diethylene glycol monoethyl ether at about 20.0% w/w; and water at about 49.59% w/w.

Another embodiment includes a composition comprising bimatoprost at about 0.1% w/w; carbomer at about 0.10% w/w; TEA at about 0.15% w/w; ethanol at about 30.0% w/w; propylene glycol at about 20% w/w; and water at about 49.7% w/w.

Another embodiment includes a composition comprising bimatoprost at about 0.1% w/w; carbomer at about 0.20% w/w; TEA at about 0.22% w/w; ethanol at about 60.0% w/w; glycerin at about 5.0% w/w; and water at about 34.48% w/w.

Another embodiment includes a composition comprising bimatoprost at about 0.1% w/w; carbomer at about 0.25% w/w; TEA at about 0.38% w/w; ethanol at about 60.0% w/w; polysorbate 20 at about 4.0% w/w; and water at about 35.27% w/w.

Another embodiment includes a composition comprising bimatoprost at about 0.1% w/w; carbomer at about 0.25% w/w; TEA at about 0.38% w/w; ethanol at about 50.0% w/w; diethylene glycol monoethyl ether at about 10% w/w; polysorbate 20 at about 4.0% w/w; and water at about 35.27% w/w.

The compositions were manufactured using the following general procedure. Non-aqueous components (e.g. bimatoprost, ethanol, glycols) were combined in a beaker and stirred using a propeller type overhead mixer until the solution was clear. Water was added to the non-aqueous mixture followed by the addition of the thickening agent. Upon dispersion of the thickening agent, a base was added to neutralize the polymer and thicken the solution into a gel.

DETAILED DESCRIPTION

Bimatoprost is a moderately soluble compound intended for topical delivery to the skin to stimulate hair growth. Hair growth includes, without limitation, stimulating the conversion of vellus hair to growth as terminal hair as well as increasing the rate of growth of terminal hair. Embodiments disclosed herein provide formulations of bimatoprost and similar compounds with penetration enhancers. These penetration enhancers facilitate active component penetration and/or maintenance at their site of action in the skin. Formulations disclosed herein can be self-preserved or contain an antimicrobial agent such as benzyl alcohol.

In accordance with embodiments disclosed herein, active components are represented by

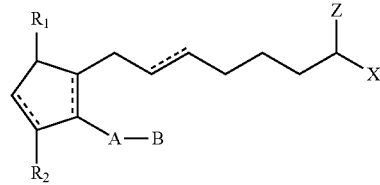

The active components are provided in particular formulations that include penetration enhancers. Some examples of representative compounds useful in the practice of embodiments disclosed herein include the compounds shown in Table 1:

TABLE 1

| Representative Compounds |
|---|
| cyclopentane heptenamide-5-cis-2-(3α-hydroxy-5-phenyl-1-trans-pentenyl)-3,5-dihydroxy, [1α,2β,3α,5α] cyclopentane N,N-dimethyl-heptenamide-5-cis-2-(3α-hydroxy-5-phenyl-1-trans-penten-yl)-3,5-dihydroxy, [1α,2β,3α,5α] |
| cyclopentane heptenylamide-5-cis-2-(3α-hydroxy-4-meta-chlorophenoxy-1-trans-pent-enyl)-3,5-dihydroxy, [1α,2β,3α,5α] |
| cyclopentane heptenylamide-5-cis-2-(3α-hydroxy-4-trifluoromethylphen-oxy-1-trans-pentenyl)-3,5-dihydroxy, [1α,2β,3α,5α] |
| cyclopentane N-isopropyl heptenamide-5-cis-2-(3α-hydroxy-5-phenyl-1-trans-pentenyl)-3,5-dihydroxy, [1α,2β,3α,5α] |
| cyclopentane N-ethyl heptenamide-5-cis-2-(3α-hydroxy-5-phenyl-1-trans-pentenyl)-3,5-dihydroxy, [1α,2β,3α,5α] |
| cyclopentane N-methyl heptenamide-5-cis-2-(3α-hydroxy-5-phenyl-1-trans-pentenyl)-3,5-dihydroxy, [1α,2β,3α,5α] |
| cyclopentane heptenamide-5-cis-2-(3α-hydroxy-4-meta-chlorophenoxy-1-trans-buteny-l)-3,5-dihydroxy, [1α,2β,3α,5α] |

In one embodiment, the compound is a cyclopentane heptanoic acid, 2-(phenyl alkyl or phenyloxyalkyl) represented by the formula II:

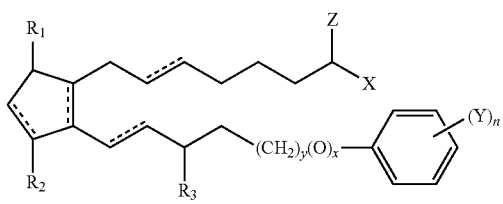

wherein y is 0 or 1, x is 0 or 1 and x and y are not both 1, Y is selected from the group consisting of alkyl, halo, e.g. fluoro, chloro, etc., nitro, amino, thiol, hydroxy, alkyloxy, alkylcarboxy, halo substituted alkyl wherein said alkyl radical comprises from one to six carbon atoms, etc. and n is 0 or an integer of from 1 to 3 and $R_3$ is =O, —OH or —O(CO)$R_6$ wherein $R_6$ is as defined above or a pharmaceutically acceptable salt thereof.

In another embodiment, the compound is a compound of formula III:

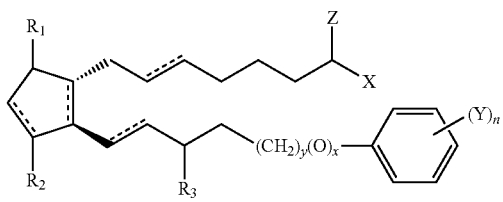

wherein hatched lines indicate a configuration, solid triangles are used to indicate β configuration. In another embodiment, y is 1 and x is 0 and $R_1$, $R_2$ and $R_3$ are hydroxy.

One exemplary compound is cyclopentane N-ethyl heptanamide-5-cis-2-(3α-hydroxy-5-phenyl-1-trans-pentenyl)-3,5-dihydroxy, [$1_\alpha, 2_\beta, 3_\alpha, 5_\alpha$], also known as bimatoprost and sold under the name of LUMIGAN® by Allergan, Inc., California, USA. This compound has the following structure:

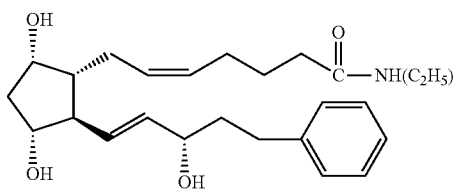

The synthesis of the above compounds has been disclosed in U.S. Pat. No. 5,607,978 which is incorporated by reference in its entirety.

Effective amounts of the active compounds can be determined by one of ordinary skill in the art but will vary depending on the compound employed, frequency of application and desired result. The compound will generally range from about $1 \times 1^{-7}$ to about 50% w/w of the composition, in one embodiment from about 0.001 to about 50% w/w of the composition and in another embodiment from about 0.1 to about 30% w/w of the composition. Ranges of within about 10-50% w/w; about 20-50% w/w; about 30-40% w/w and about 35% are also included.

The pharmaceutical formulations disclosed herein can include one or more penetration enhancers. The phrase "penetration enhancers" includes any agent that facilitates the transfer of active components to their site of action or maintains them at their site of action. Non-limiting examples of classes of appropriate penetration enhancers include alcohols, glycols, fatty acids, ethers, esters, occlusive agents and surface active agents. Representative examples of these classes are provided below.

Alcohols include, without limitation, ethanol, propanol, N-propanol, isopropanol, butyl alcohol, octanol, benzyl alcohol and acetyl alcohol, in one embodiment, as described in U.S. Pat. No. 5,789,244, the entire contents of which are incorporated by reference herein. Fatty alcohols include, for example, stearyl alcohol and oleyl alcohol.

Glycols include, without limitation, glycerine, propyleneglycol, polyethyleneglycol and other low molecular weight glycols such as glycerol and thioglycerol.

Fatty acids, esters and ethers include, without limitation, oleic acid, palmitoleic acid, straight chain $C_4$-$C_{20}$ saturated monocarboxylic and dicarboxylic acids, octanoic and decanoic acids, methyl laurate, ethyl oleate, polyethylene glycol monolaurate, propylene glycol monolaurate, propylene glycerol dilaurate, glycerol monolaurate, glycerol monooleate, isopropyl n-decanoate, octyldodecyl myristate, diethylene glycol monoethyl ether, diethylene glycol monomethyl ether and compounds wherein a $C_2$-$C_4$ alkane diol or triol is substituted with one or two fatty ether substituents.

Occlusive agents include, without limitation, silicones, mineral oils and greases, long chain acids, animal fats and greases, vegetable fats and greases, water insoluble polymers, paraffin, paraffin oil, liquid paraffin, petrolatum, liquid petrolatum, white petrolatum, yellow petrolatum, microcrystalline wax and ceresin.

Surface active agents include without limitation, polysorbate 20, 40, 60 and 80, TWEEN® (20, 40, 60, 80), POLOXAMER® (231, 182, 184), sodium dodecyl sulfate (SDS), lecithin, lysolecithin, nonylphenoxypolyoxyethylene, lysophosphatidylcholine, polyethylenglycol 400, polyoxyethylene ethers, polyglycol ether surfactants, DMSO, sodium laurate, sodium lauryl sulfate, cetyltrimethylammonium bromide, and benzalkonium chloride.

Additional penetration enhancers will be known to those of ordinary skill in the art of topical drug delivery, and/or are described in the pertinent texts and literature.

Embodiments disclosed herein can also include viscosity increasing agents. Appropriate agents include, without limitation, methylcellulose, polyvinyl alcohol, polyvinyl pyrrolidone, hyaluronic acid and chondroitin sulfate.

Certain embodiments disclosed herein can include preservatives including, without limitation, benzyl alcohol, benzalkonium chloride, chlorhexidine, chlorobutanol, methyl-, propyl-, or butyl-parahydroxybenzoic acids, phenylmercuric salts including, without limitation, nitrate, chloride, acetate, and borate and betain.

Various other additives may be included in the compositions of the present invention in addition to those identified above. These include, but are not limited to, antioxidants, astringents, perfumes, emollients, pigments, dyes, humectants, propellants, and sunscreen agents, as well as other classes of materials whose presence may be cosmetically, medicinally or otherwise desirable. The compositions and formulations may also be taken in conjunction with minoxidil and propecia.

Compositions can also be formulated as "slow-releasing" formulations so that the activity of active components is sustained for a longer period of time between treatments.

While particular embodiments disclosed herein can include each of the components discussed above, other particular embodiments can be required to be "substantially free" of one or more of these components in various combinations. "Substantially free", as used herein, means that the component is not added to a formulation and cannot be present in any amount greater than about 1% w/w.

While not limiting the scope of express exclusion of the preceding paragraph, particular embodiments disclosed herein can be substantially free of one or more of bimatoprost, carbomer, NaOH (s), TEA, ethanol, glycerin, diethylene glycol, monoethyl ether, propylene glycol, polysorbate 20, polysorbate 40, polysorbate 60, polysorbate 80, PPG-5 ceteth-20, oleic acid, isostearyl isostearate, isopropyl myristate, dipropylene glycol dimethyl ether, diethylene glycol, dipropylene glycol, triglycerides, caprylic/capric, benzyl alcohol, silicone and water.

All components of formulations described herein will be included in amounts that are dermatologically-acceptable. As used herein, "dermatologically-acceptable" means that the compositions or components thereof are suitable for use in contact with human skin without undue toxicity, incompatibility, instability, allergic response, and the like. As used in herein as applied to active agents and excipients, the term "about" refers to variations in concentrations which are considered to be bioequivalent.

Embodiments disclosed herein find application in mammalian species, including both humans and animals. In humans, the compounds of embodiments disclosed herein can be applied without limitation, to the scalp, face, beard, head, pubic area, upper lip, eyebrows, and eyelids. The compositions of the present inventions may be used for treating various hair loss disorders including but not limited to alopecia greata, telogen effluvium, anagen effluvium, cicatricial alopecia and scarring alopecia; hair shaft abnormalities such as trichorrexis nodosa, loose anagen syndrome, trichotillomania and traction alopecia; infectious hair disorders such as tiniea capitis, sebohorreic dermatitis, and follicullitus of the scalp; genetic disorders such as androgenetic alopecia and patients undergoing hair loss due to chemotherapy, hormonal imbalance (e.g., thyroid conditions such as hypothyroidism and hyperthyroidism, pregnancy, child birth, discontinuation of birth control pills and changes in menstrual cycle), fungal infection of the scalp such as ringworm, medicines which cause hair loss such as anti-coagulants, medicine for gout, depression, high blood pressure and certain heart medications. The formulations of the present invention may be used to treat hair loss related to other disease such as diabetes, lupus, and poor nutrition, mental and physical stress such as due to surgery, illness and high fever. Environmental factors and chemicals used in hair treatment (dying, tinting and bleaching).

In animals raised for their pelts, e.g., mink, the formulations can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The compositions and methods of the present invention may be applied to patients suffering from hair loss or in healthy patients simply wanting to increase hair growth in any part of the body.

The compositions disclosed herein are formulated for topical administration. The term "topical administration" as used herein includes applying a formulation as described herein to the outer skin or hair. The application will generally occur at or near the area of desired hair growth.

Accordingly, appropriate formulation or composition types include, without limitation, solutions, gels, ointments, foams, films, liniments, creams, shampoos, lotions, pastes, jellies, sprays and aerosols. Such formulation types can be applied in swaths, patches, applicators or through the use of impregnated dressings depending on the situation and part of the body to be treated.

Typically, the formulations described herein will be applied repeatedly for a sustained period of time to the part of the body to be treated. In particular embodiments, formulations disclosed herein can include one or more applications daily, one or more applications weekly, one or more applications monthly or one or more applications yearly for a period of treatment of at least one day, at least one week, at least one month, at least one year or until the treatment has achieved or achieved and maintained a desired result.

Formulations described herein will be administered in safe and effective amounts. As used herein, "safe and effective amounts" include an amount sufficient so that the composition provides the desired hair growth stimulation effect at a reasonable benefit/risk ratio attendant with any medical treatment. Within the scope of sound medical judgment, the amount of active components used can vary with the particular condition being treated, the severity of the condition, the cause of the condition, the duration of the treatment, the specific active component employed, its concentration, the specific vehicle utilized, the general health of the patient, the tolerance of the patient to various effects of the administration, other drugs being administered to the patient, and like factors within the specific knowledge and expertise of the patient or attending physician.

For daily administration, an appropriate dose can include, without limitation, about 0.1 ng to about 100 mg, about 1 ng to about 10 mg per day or in another embodiment about 10 ng to about 1 mg per day.

Non-limiting examples of some components with their appropriate concentration ranges and function are provided in Table 1 below. Particular examples of non-limiting formulations or compositions are provided in Table 2.

TABLE 1

Example Components with Function and Concentration Ranges

| Ingredient | Function | Composition (% w/w) |
|---|---|---|
| bimatoprost | Active | 0.03-1.0 |
| carbomer | Thickener | 0.05-1.0 |
| base | Neutralizing Agent | 0.01-2.0 |
| ethanol | Penetration | 10-90 |
| glycerin | enhancers | 1.0-20 |
| diethylene glycol monoethyl ether | | 1.0-50 |
| propylene glycol | | 1-50 |
| polysorbate 20 | | 0.1-5.0 |
| polysorbate 40 | | 0.1-5.0 |
| polysorbate 60 | | 0.1-5.0 |
| polysorbate 80 | | 0.1-5.0 |
| PPG-5 ceteth-20 | | 0.1-5.0 |
| oleic acid | | 0.1-5.0 |
| isostearyl isostearate | | 0.1-10 |
| isopropyl myristate | | 0.1-10 |
| dipropylene glycol dimethyl ether | | 1-50 |
| diethylene glycol | | 1-50 |
| dipropylene glycol | | 1-50 |
| caprylic/capric triglycerides | | 0.1-10 |
| benzyl alcohol | Preservative | 0.1-2.0 |
| silicone | Occlusive Agent | 0.1-10 |
| water | Vehicle | 0-90 |

TABLE 2

Example Compositions

| Ingredient | Function | Composition (% w/w) | | | | | | |
|---|---|---|---|---|---|---|---|---|
| bimatoprost | Active | 0.1 | 0.1 | 0.1 | 0.1 | 0.1 | 0.1 | 0.1 |
| carbomer | Thickener | 0.10 | 0.15 | 0.125 | 0.10 | 0.20 | 0.25 | 0.25 |
| NaOH (s) | Neutralizing Agent | 0.035 | | | | | | |
| TEA | Neutralizing Agent | | 0.22 | 0.18 | 0.15 | 0.22 | 0.38 | 0.38 |
| ethanol | Penetration enhancers | 15.0 | 15.0 | 30.0 | 30.0 | 60.0 | 60.0 | 50.0 |
| glycerin | | | | | | 5.0 | | |
| diethylene glycol monoethyl ether | | 10.0 | 10.0 | 20.0 | | | | 10 |
| propylene glycol | | | | | 20 | | | |
| polysorbate 20 | | | 4.0 | | | | 4.0 | 4.0 |
| water | Vehicle | 74.8 | 70.5 | 49.595 | 49.7 | 34.48 | 35.27 | 35.27 |

EXAMPLE I

Preparations of Bimatoprost Scalp Hair Growth Gel Compositions

Ethyl alcohol is weighed into a suitable media jar equipped for mixing, bimatoprost is then added to the ethyl alcohol and stirred at moderate speed until bimatoprost is dissolved. Into separate mixing tank water for injection, glycerin, diethylene glycol monoethyl ether, and propylene glycol are added and mixed until the solvents are dispersed. Ethyl alcohol/bimatoprost solution is then added into the water mixture and mixed until the components are homogenously mixed (about 5 minutes of mixing). To the above mixture the carbomer thickener is added and mixed until well dispersed, once dispersed a base is added to thicken the solution into a gel. Representative formulations made according to the method above are shown in Table 3 below.

TABLE 3

Bimatoprost Scalp Hair Growth Topical Gel Formulations

| Ingredient (% w/w) | Function | Bimatoprost 0.03% (Propylene Glycol) Solution | Bimatoprost 0.1% (Propylene Glycol) Solution | Bimatoprost 0.3% (Propylene Glycol) Solution | Bimatoprost 0.2% (Propylene Glycol) Solution |
|---|---|---|---|---|---|
| Bimatoprost | Active | 0.03 | 0.1 | 0.3 | 0.2 |
| Propylene glycol | Penetration enhancer | 10.0 | 10.0 | 10.0 | 10.0 |
| Diethylene glycol monoethyl ether | | 10.0 | 10.0 | 10.0 | 10.0 |
| Ethyl alcohol | | 30.0 | 30.0 | 30.0 | 30.0 |
| Glycerin | | 2.0 | 2.0 | 2.0 | 2.0 |
| Carbomer (Ultrez 10) | Thickener | 0.15 | 0.15 | 0.15 | 0.15 |
| Triethanolamine | Neutralizing agent | 0.16 | 0.16 | 0.16 | 0.16 |
| Purified water | Vehicle | 47.66 | 47.59 | 47.39 | 47.49 |

EXAMPLE II

In Vivo Treatment

A study is initiated to systematically evaluate the appearance of hair on the scalp and eyebrows who are administered bimatoprost gel formulations as in Table 3. The study involves 10 subjects, 5 male, 5 female, average age 70 years, (ranging from 50-94 years). Each subject is treated daily by the topical application of bimatoprost by the 0.3% w/w bimatoprost formulation of Table 3.

The study is limited to subjects who have administered bimatoprost for more than 3 months. The mean duration of exposure to the 0.3% w/w bimatoprost gel formulation prior to assessing the parameter of hair or eyebrow growth between the control and study eye is 129 days (range 90-254 days). Observations are made under high magnification at a slit lamp biomicroscope. Documentation of differences between the control and treatment areas is accomplished using a camera specially adapted for use with a slit lamp biomicroscope.

The Results of the Observations Will be as Follows:

Length of hair and eyebrows: Increased length of hair in both groups is regularly observed. The difference in length varies from approximately 10% to as much as 30%.

Number of hairs and eyebrows: Increased numbers of hairs are observed on the scalp and eyebrows of each patient. The difference in number of hair and eyebrows varies from approximately 5% to as much as 30%. Whether statistically significant or not, bimatoprost with a penetration enhancer will provide better and/or faster results than bimatoprost without a penetration enhancer.

The foregoing observations will establish that 0.03% w/w bimatoprost composition penetrates skin and grows hair.

EXAMPLE III

Topical Cream

A topical 0.2% w/w bimatoprost cream is prepared as follows: Tegacid and spermaceti are melted together at a temperature of 70-80° C. Methylparaben is dissolved in about 500 gm of water and propylene glycol, polysorbate 80, bimatoprost and a penetration enhancer are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

EXAMPLE IV

Topical Cream

A 0.1% w/w bimatoprost topical cream is prepared as follows: Tegacid and spermaceti are melted together at a temperature of 70-80° C. Methylparaben is dissolved in water and propylene glycol, polysorbate 80, bimatoprost and a penetration enhancer are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

EXAMPLE V

Topical Ointment

An Ointment Containing 2.0% w/w Bimatoprost is Prepared as Follows:

White petrolatum and wool fat are melted, strained and liquid petrolatum is added thereto. Bimatoprost, a penetration enhancer, zinc oxide, and calamine are added to the remaining liquid petrolatum and the mixture milled until the powders are finely divided and uniformly dispersed. The mixture is stirred into the white petrolatum, melted and cooled with stirring until the ointment congeals. In other variants, the zinc oxide and/or calamine can be omitted such that the formulation is substantially free of the zinc oxide or calamine.

EXAMPLE VI

Ointment

An ointment containing 5% w/w bimatoprost and a penetration enhancer is prepared by adding the active compound to light liquid petrolatum. White petrolatum is melted together with wool fat, strained, and the temperature adjusted to 45-50° C. The liquid petrolatum slurry is added and the ointment stirred until congealed. The ointment can be packaged in 30 gm tubes.

EXAMPLE VII

Spray Formulation

An aqueous spray formulation containing 0.03%, w/w bimatoprost and a penetration enhancer are prepared as follows. Bimatoprost and a penetration enhancer are dissolved in water and the resulting solution is sterilized by filtration. The solution is aseptically filled into sterile containers with a spray nozzle for application on top of the head. The formulation is as follows:

TABLE 4

Bimatoprost Spray Formulation of Example VII

| Ingredient (% w/w) | Function | Spray formulation |
|---|---|---|
| Bimatoprost | Active | 0.03 |
| Propylene glycol | Penetration | 5 |
| Diethylene glycol monoethyl ether | enhancer | 5 |
| Ethyl alcohol | | 15 |
| Light mineral oil | | — |
| Ceteareth 12 | | — |
| Glycerin | | 1 |
| Carbomer (Ultrez 10) | Thickener | — |
| Triethanolamine | Neutralizing agent | — |
| Purified water | Vehicle | 24 |
| Hydrofluoro carbon, hydrocarbon propellant, $CO_2$, or, Nitrogen | Propellant | 49.97 |

EXAMPLE VIII

Lotion

A sample of bimatoprost and a penetration enhancer is dissolved in the vehicle of N-methylpyrrolidone and propylene glycol to make a 0.5% w/w bimatoprost lotion for application to the scalp or other parts of the body for growing hair.

EXAMPLE IX

Aerosol

An aerosol containing approximately 0.1% w/w bimatoprost and a penetration enhancer is prepared by dissolving the bimatoprost and a penetration enhancer in absolute alcohol. The resulting solution is filtered to remove particles and lint. This solution is chilled to about −30° C. A chilled mixture of dichlorodifluoromethane and dichlorotetrafluoroethane is then added to the solution. Thirteen ml plastic-coated amber bottles can be cold filled with 11.5 gm each of the resulting solution and capped. The aerosol may be sprayed onto the scalp or other parts of the body to grow hair.

EXAMPLE X

Topical Foam Formulation

A 0.1% w/w bimatoprost topical foam formulation is prepared as follows: Methylparaben is dissolved in about 500 gm of water and propylene glycol, polysorbate 80, bimatoprost and a penetration enhancer are added in turn, maintaining a temperature of 75-80° C. The methylparaben mixture is added slowly to Tegacid and spermaceti, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

An alternative foam formulation prepared in a similar manner as taught in Example X in Table V is as follows:

| Ingredient (% w/w) | Function | Foam formulation |
|---|---|---|
| Bimatoprost | Active | 0.03 |
| Propylene glycol | Penetration | — |
| Diethylene glycol monoethyl ether | enhancer | 5 |
| Ethyl alcohol | | 10 |
| Light mineral oil | | 6 |

| Ingredient (% w/w) | Function | Foam formulation |
|---|---|---|
| Ceteareth 12 | | 5 |
| Glycerin | | — |
| Carbomer (Ultrez 10) | Thickener | — |

EXAMPLE XI

Dusting Powder

A powder of the compound bimatoprost and a penetration enhancer is prepared by mixing in dry form with talcum powder at a weight/weight ratio of 1:1:10.

EXAMPLE XII

Related Compounds

Following the procedures of the preceding Examples, compositions are similarly prepared substituting an equimolar amount of a compound of Table 1 for the bimatoprost disclosed in the preceding Examples.

Unless otherwise indicated, all numbers expressing quantities of ingredients, properties such as molecular weight, reaction conditions, etc. used in the specification and claims are to be understood as being modified in all instances by the term "about." "About" refers to variations in concentrations of excipients and types of excipients which are considered to be bioequivalent according to the FDA and other regulatory authorities.

EXAMPLE XIII

A 44 year old Caucasian male undergoing hair loss due to alopecia greata applies once daily before sleeping the 0.1% w/w bimatoprost composition of Table 3 for a period of 6 months. After 3 months of application, the subject will notice new hair growth where there previously had been none and darkening of the follicles of old hair. Observations of new hair growth are made under high magnification at the slit lamp biomicroscope and by computer assisted image analysis. Documentation of differences between the control and treatment areas is accomplished using a camera specially adapted for use with the slit lamp biomicroscope.

Example XIV

A 37 year old Hispanic male suffering from male pattern baldness due to androgenetic alopecia applies the 0.2% w/w bimatoprost composition of Table 3 twice daily in areas where hair is noticeably thinning. After 63 days of application, increased growth of hair will be noticed as will be new hair growth as measured by high magnification at the slit lamp biomicroscope and by computer assisted image analysis. After satisfactory levels of hair growth are observed, the patient applies the 0.2% w/w bimatoprost composition only twice a week.

EXAMPLE XV

A 29 year old Caucasian healthy female wishes to have fuller hair and more hair growth even though no disease or hair loss condition has been diagnosed by doctors. The patient will apply the 0.3% w/w bimatoprost composition of Table 3 once daily until more hair growth is observed after approximately three months of use. The patient continues to apply the composition once a week to maintain the increased hair growth.

EXAMPLE XVI

A 35 year old African American male diagnosed with follicular degeneration syndrome and associated hair loss will apply the 0.03% w/w bimatoprost composition of Table 3. The composition will be applied twice daily, once in the morning after showering and once in the evening. After 46 days of application, increased hair growth will be noticed and easing of the symptoms of follicular degeneration syndrome. The patient continues application for another 6 months.

What is claimed is:

1. A composition for growing hair by topical application comprising:
    at least one penetration enhancer; and
    0.01% to 5% w/w bimatoprost;
    wherein said composition is formulated for topical administration to the skin;
    wherein the penetration enhancer comprises a combination of a first penetration enhancer group comprising ethanol, propylene glycol, and diethylene glycol monoethyl ether; and a second penetration enhancer group comprising an effective amount of at least two compounds selected from the group consisting of glycerol monooleate, oleic acid, and benzyl alcohol.

2. The composition of claim 1 wherein the composition comprises 1% w/w bimatoprost.

3. The composition according to claim 1 wherein the composition is in the form of one selected from the group consisting of solutions, gels, ointments, foams, films, liniments, creams, shampoos, lotions, pastes, jellies, sprays and aerosols.

4. The composition of claim 3 wherein the composition is packaged in a kit with an applicator for application to the skin.

5. A method for stimulating hair growth comprising topically administering a composition comprising:
    at least one penetration enhancer; and
    bimatoprost;
    wherein said composition is formulated for topical administration to the skin;
    wherein the penetration enhancer comprises a combination of a first penetration enhancer group comprising ethanol, propylene glycol, and diethylene glycol monoethyl ether; and a second penetration enhancer group comprising an effective amount of at least two compounds selected from the group consisting of glycerol monooleate, oleic acid, and benzyl alcohol.

6. The method according to claim 5 comprising bimatoprost at a concentration of about 0.03% w/w to about 5% w/w.

7. The method according to claim 5, wherein the composition is applied at least once daily to the scalp.

8. The method according to claim 5, wherein the composition is applied at least once daily to the scalp for treatment of one of the following conditions selected from the group consisting of alopecia areata, telogen effluvium, anagen effluvium, cicatricial alopecia, scarring alopecia; hair shaft abnormalities, trichorrexis nodosa, loose anagen syndrome, trichotillomania, traction alopecia; infectious hair disorders, tinica capitis, seborrheic dermatitis, folliculitus of the scalp, and androgenetic alopecia.

9. The method according to claim 5 wherein the composition is applied at least once a day to both the scalp and the eyebrows for patients experiencing hair loss due to chemotherapy, hormonal imbalance, fungal infection of the scalp, anti-coagulants, medicine for gout, depression, high blood pressure and heart disease.

10. The composition of claim 1, wherein the second penetration enhancer group comprises glycerol monooleate, oleic acid, and benzyl alcohol.

11. The method of claim 5 comprising bimatoprost at a concentration of 0.3% w/w.

12. The method of claim 5 comprising bimatoprost at a concentration of 1% w/w.

13. The method of claim 5, wherein the second penetration enhancer group comprises glycerol monooleate, oleic acid, and benzyl alcohol.

* * * * *